(12) United States Patent
Itoman et al.

(10) Patent No.: US 6,190,417 B1
(45) Date of Patent: Feb. 20, 2001

(54) FEMORAL PROSTHESIS DEVICE

(75) Inventors: Moritoshi Itoman, Yamato; Kiyoshi Mabuchi, Sagamihara; Noriyuki Ishida, Kyoto; Shingo Tamabuchi, Kyoto; Masaru Ueno, Kyoto, all of (JP)

(73) Assignee: Kyocera Corporation, Kyoto (JP)

( * ) Notice: Under 35 U.S.C. 154(b), the term of this patent shall be extended for 0 days.

(21) Appl. No.: 09/356,849

(22) Filed: Jul. 19, 1999

(51) Int. Cl.⁷ ........................................................ A61F 2/36
(52) U.S. Cl. ..................... 623/23.15; 623/23.26; 623/23.27; 623/20.36; 623/22.4
(58) Field of Search ............................. 623/23.15, 16.11, 623/23.26, 23.27, 23.29, 23.33, 23.44, 22.4, 22.43, 22.44, 22.45, 22.46, 20.36, 23.21, 23.31; 606/64

(56) References Cited

U.S. PATENT DOCUMENTS

| | | | |
|---|---|---|---|
| 3,466,670 | * | 9/1969 | Christiansen ...................... 623/23.15 |
| 4,623,349 | * | 11/1986 | Lord .................................. 623/18.11 |
| 4,895,572 | * | 1/1990 | Chernoff ........................... 623/23.15 |
| 5,002,578 | * | 3/1991 | Luman .............................. 623/23.15 |
| 5,702,484 | * | 12/1997 | Goymann et al. ................ 623/23.15 |

FOREIGN PATENT DOCUMENTS

| | | | |
|---|---|---|---|
| 41 29 724 | 3/1993 | (DE) . | |
| 43 20 086 | 12/1994 | (DE) . | |
| 43 36 819 | 3/1995 | (DE) . | |
| 0 198 163 | 10/1986 | (EP) . | |
| 0 567 349 | 10/1993 | (EP) . | |
| 1416534 | * | 9/1965 | (FR) ................................. 623/23.15 |
| 1 416 534 | 1/1966 | (FR) . | |
| 63-105759 | 5/1988 | (JP) . | |
| 63-105758 | * | 5/1988 | (JP) ................................. 623/23.15 |
| 63-164946 | 7/1988 | (JP) . | |
| 63-164947 | 7/1988 | (JP) . | |
| 63-212350 | 9/1988 | (JP) . | |
| 63-212351 | 9/1988 | (JP) . | |
| 63-212352 | 9/1988 | (JP) . | |
| 63-272345 | 11/1988 | (JP) . | |
| 2-041153 | 2/1990 | (JP) . | |
| 11 206794 | 8/1999 | (JP) . | |

* cited by examiner

Primary Examiner—Philogene Pedro
(74) Attorney, Agent, or Firm—Hogan & Hartson, LLP.

(57) ABSTRACT

The present invention provides a femoral prosthesis to be utilized as an implant into a human femur to connect the coxa. The femoral prosthesis comprises a stem body to be inserted into a femur bone, a neck portion fixed integrally at the proximal portion of the stem body, a spherical head member having an opening to receive the neck potion, and a cross pin for fixing the stem body to the femur bone, wherein the stem body is formed with a pinnig hole through a proximal portion thereof corresponding to a greater trochanter of the femur bone, and the cross pin is in a unthreaded cylindrical shape and inserted into the pinning hole, both ends of the cross pin being projected out of the stem body to be engaged with the bone wall of the femur bone.

9 Claims, 4 Drawing Sheets

FEMORAL PROSTHESIS DEVICE

BACKGROUND OF THE INVENTION

1. Field of the Invention

The present invention relates to a femoral prosthesis for applying to a human body.

2. Prior Art

Conventionally, artificial hip joints have been composed of a socket inserted into the pelvic bone and a femoral prosthesis which has a stem and a spherical head at the end capable of rotatably engaging the socket.

Generally, the stem, made of a metal such as stainless steel or cobalt-chromium alloy, is inserted into a femoral canal and fixed by using cementing compound between the stem and the canal wall. On the acetabular side, the socket is cemented to a pelvic bone, which receives the spherical head of the stem.

Particularly, the stem is inserted deeply within the elongated canal of the femur, and when the artificial joint is loaded, some difference in Young's modulus between the metal stem and the bone tissue causes different amounts of then deformation, then leading to a sinking of the stem into the bone due to relaxation between the cement compound and the bone or between the metal stem and the bone. This results in losing joint function through looseness between the members or, in the extreme case, separation of the stem form the femoral cavity.

Attempts have been made to prevent the looseness between the cement and bone or the metal stem. For example, the stem material has been made from to titanium or titanium alloy instead of stainless steel or Co—Cr alloy, to approximate the Young's modulus of the stem to that of the bone tissue. This attempt failed to completely resolve the looseness problem.

Another improvement has been attempted, in which the stem is formed such that the outside of the stem approaches to inner dimensions of the, to make the gap between the stem surface and the bone canal as narrow as possible and, then inserting the stem into the bone without use of any cementing compound. It was, however, difficult to configure the stem in a shape to accurately duplicated to the inner canal profile. Practically, sufficient products, except in the case of custom-ordered products, have not been available because of patients having great difference in inner femoral profiles.

Recently, in another attempt, U.S. Pat. No. 4,895,571 describes a interlocking femoral prosthesis utilizing surgical screws which pass through the openings formed through the stem, which fix the stem directly to the femoral cavity without use of the cement material.

The screw comprises a straight portion and a wider threaded portion with a greater length than the straight portion, and, on the other hand, the opening formed within the prosthesis stem is set to have a inner diameter wide enough to pass the threaded portion of the screw therethrough, resulting in loose gaps between the screw and the inner wall of the opening. This method can cause severe mechanical instability problems of relative movement, such as micro-movement, of the stem with regard to the bone.

SUMMARY OF THE INVENTION

Considering the above problems inherent in prior art, an object of the invention is to provide a femoral prosthesis having a stem body for a long lifetime to be implanted within a femur bone, wherein the stem body is capable of being fixed within the femur bone by using a system for relaxing the stress loaded onto the femur bone to make the bone and the stem body bend easily when force is applied to the femoral prosthesis and the femur bone.

In the present invention, the femoral prosthesis having a stem body comprises a pinning hole perpendicular to the axis of the stem body, at a portion of a greater trochanter which is formed through the stem body, and a cylindrical cross pin passing through the pinning hole with ends of the pin projecting out of the stem body.

Particularly, the stem body at either side is implanted into the femur so the pinning hole of the stem body is inserted within the femoral canal and a cross pin is inserted into the pinning hole through openings formed through the bone wall so that the cross pin can fix the stem body to the bone preventing even slight movement between the femoral bone and the stem body.

The femoral prosthesis according to the present invention includes a stem body having a specific configuration at its distal potion in order to achieve attachment of said stem body portion to bone tissue which will have grown inside the femoral canal. particularly, the distal portion of the stem body may be corrugated with a plurality of edges and as many grooves alternatingly and longitudinally aligned outside. This configuration of the stem body can promote the anchoring effect of the stem body due to the bone tissue growth and extension.

The femoral prosthesis in accordance with the present invention can be advantageously utilized not only for a replacement of a upper part of a femur bone, for example for healing a failure of the head of femur, but also for a total hip replacement in conjunction with a hip prosthesis.

BRIEF DESCRIPTION OF THE DRAWINGS

The present invention is described in further detail below, referring to the accompanying drawings, in which.

DETAILED DESCRIPTION OF THE PREFERRED EMBODIMENTS

Figure 1:
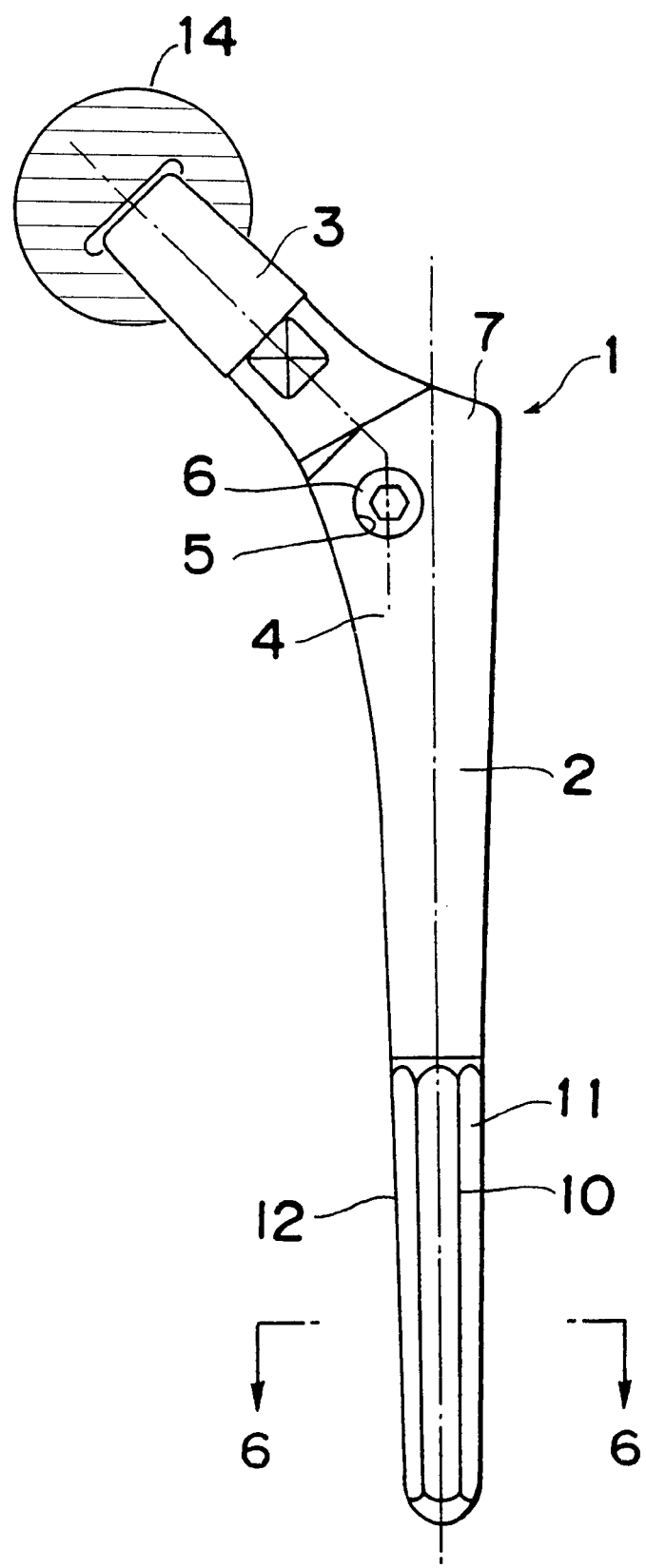
FIG. 1 shows a side view of a femoral prosthesis according to a embodiment of the present invention.
Figure 2:
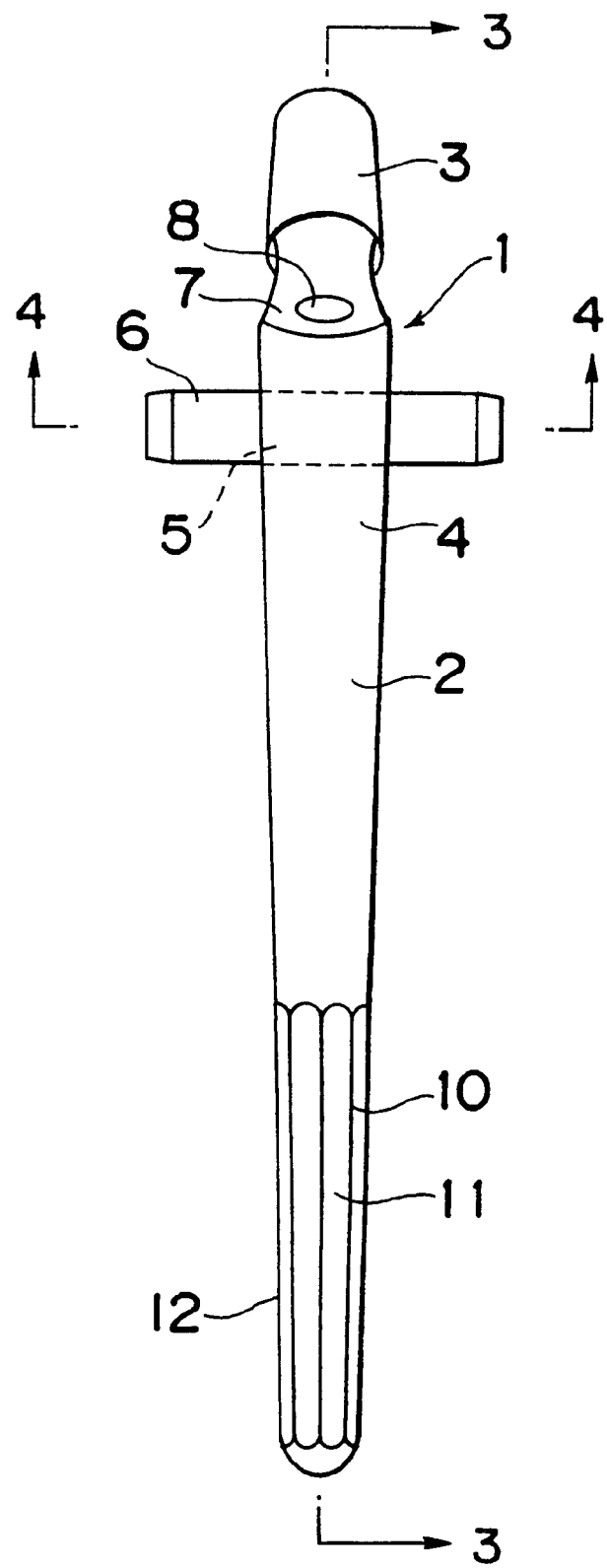
FIG. 2 shows a front view of the a femoral prosthesis shown in FIG. 1.

The femoral prosthesis comprises: a stem member having stem body to be implanted into the femoral bone, which is provided with a neck portion with a tapering shape on a shoulder portion of the stem member; a spherical head member 14 having an opening capable of receiving the neck portion; and, a cross pin being capable of fixing the stem body to the femoral bone.

The stem member 1 has a stem body 2 which is slightly tapered toward its distal portion in a shaft like shape for insertion into a femoral bone (not shown), The stem member 1 may be formed of metal material harmless to the human body, such as pure titanium, a titanium alloy or a cobalt-chromium alloy.

In the invention, there is formed a pinning hole 5, i.e. a through hole formed through the stem body 2, which is located at the trochanter portion 4 of the stem body 2, i.e., an upper portion corresponding to a greater trochanter of the femur bone. The pinning hole may be substantially perpendicular to the longitudinal axis of the stem body 2.

A cross pin 6 is designed to be a unthreaded cylinder capable of inserting into the pinning hole 5 of the stem body 2 with either end projected from the outsides of the stem body by the depth of the femur bone.

In the invention the femoral prosthesis is implanted within the femur such that the stem body 2 is inserted into the femoral canal, the cross pin being inserted into the pinning hole 5 formed through the stem body 2 via openings (not shown) in the bone wall of the femur, the projected end portions of the cross pin 6 becoming engaged in the bone wall, to secure the femoral prosthesis to the femur bone.

Furthermore, in the implantation process of utilizing the cross pin 6 for fixation between the prosthesis and a femur bone, firstly, the femoral prosthesis is positioned to a bone by driving the stem body 2 into the femoral canal of the femur bone. The stem body 2 having in advance been provided with the pinning hole which is positioned at some predetermined length from a reference point such as a shoulder portion of the stem body or a specific point on the neck portion 3.

Second, after insertion of the stem member into the femur bone, there is formed openings in the wall of the femur bone by drilling such that the openings of the bone wall can be connected by the pinning hole 5 of the stem body 2. In this step, a specified drill guide may preferably be utilized, having a guide hole for guiding a drill shaft, the drill guide being attached to the neck portion or shoulder portion exposed at the top end of the bone, then, positioning a drill to aim along the center line of the pinning hole. A drill is advanced from one point outside the femur bone toward the center of the pinning hole 5 of the stem body 2, first boring to form an opening, and next, passing through the pinning hole 5, and lastly boring through another diametrically opposed point of the wall of the femur bone to form another opening through the femur bone. This procedures can result in one perfect pinning hole which passes through both the wall openings of the femur bone and the pinning hole 5 of the stem body 2 inserted within said bone.

Third, the cross pin 6 is inserted from one of the openings of the bone to the other by way of the pinning hole of the stem body 2. Thus, this pinning system body 2 can firmly connect the femoral prosthesis to the femur.

Thereafter, a spherical head member is connected to the top of the neck portion 3 of the stem member 1 during a common surgical practice.

The above embodiment has shown the spherical head member as a separate piece, which is separated from the stem member. This type of spherical head member is advantageous in that it is possible to prepare spherical head member dimensions and profiles independently from the stem members. In the present devices a spherical head member may be previously affixed integrally to the stem member the neck portion to composing a femoral prosthesis.

In the present invention, the femoral prosthesis may utilize a means for preventing the cross pin 6 from being removed and otherwise displacing inside the pinning hole 5 of the stem body 2 which is connected to the femur bone during the medical healing and also during practical using of the prosthesis after the healing.

Figure 3:
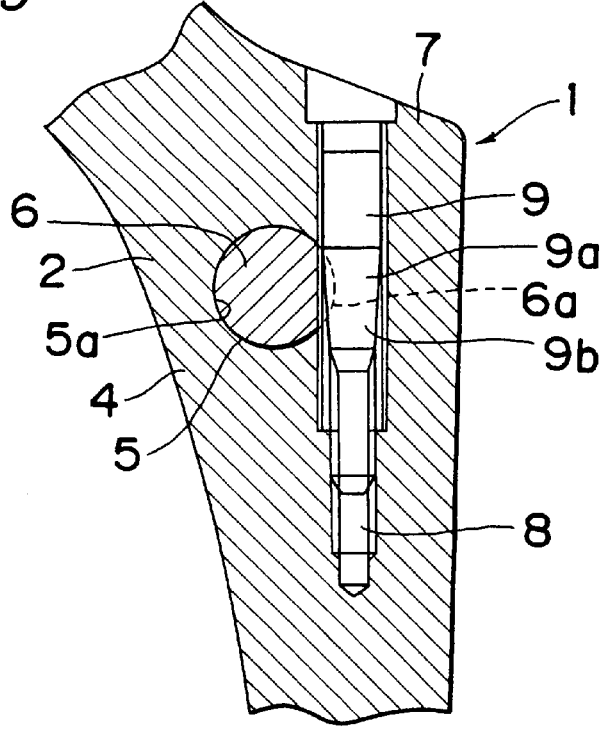
FIG. 3 shows a elongated sectional view of the femoral prosthesis, which is seen along the arrows A—A shown in FIG. 1.

Said means for preventing the pin movement may comprise a bolt hole 8 which is formed into the stem body 2 below from a shoulder point 7 of the stem body 2 as shown in FIG. 3, so that the bolt hole 8 can reach or cross the pinning hole 5 in the stem body, and a bolt 9 can be inserted through the bolt hole 8, an end portion of the bolt 9 being capable of engaging the cross pin 6 inserted in the pinning hole 5.

Figure 4:
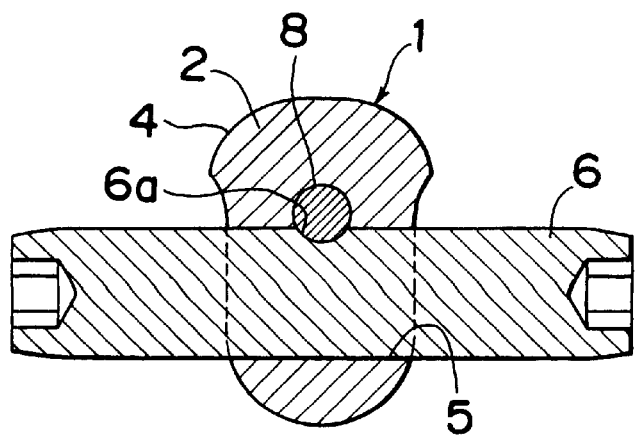
FIG. 4 shows a elongated sectional view of the femoral prosthesis, which is seen along the arrows B—B shown in FIG. 1.

Particularly, the axis of the bolt hole 8 may be deviated from the axis of the pinning hole 5 such that the bolt in the bolt hole 8 can cut in part cross the pinning hole 5. In this case, as shown in FIG. 4, the cross pin 6, in a unthreaded, cylindrical shape, may preferably be formed with a notch 6a or a groove in a part of the round surface at the mid point of its length. The notch 6a is formed capable of in part receiving a part of the surface of the bolt when inserted in the pinning hole 5. When screwed into the bolt hole 8, the bolt 9 is engaged in the notch 6a on the cross pin 6 which has been inserted within the pinning hole 5, preventing movement of the cross pin 6 inside the pinning hole 5. Thus, the positioning of the cross pin 6 is completed at a fixed location, enabling the femoral prosthesis to be secured to the femur bone.

Figure 5:
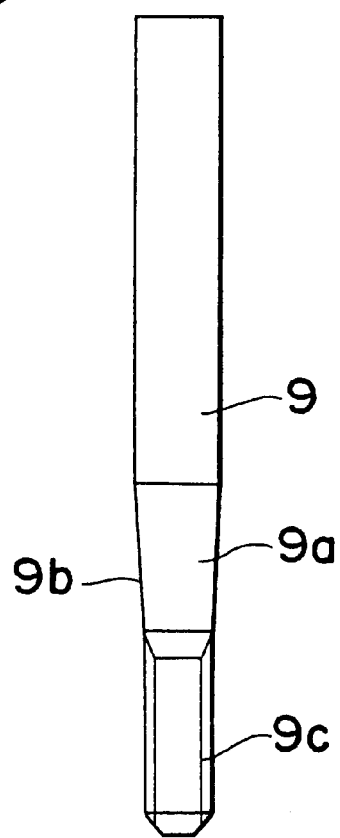
FIG. 5 shows a side view of a bolt to be inserted into the femoral prosthesis for fixing the cross pin, according to an embodiment of the invention; and, FIG. 6 shows a cross sectional view of a distal portion of a stem body of the femoral prosthesis according to an embodiment of the present invention.

Additionally, as shown in FIG. 5, the bolt is cylindrically tapered at the middle portion 9a and threaded at the further end portion 9c, wherein when the bolt 9 is screwed down into the bolt hole 8, the tapered periphery 9b of the middle portion 9a can generate great force to press the cross pin 6 toward a opposite hole wall 5a in the pinning hole 5 of the stem body 2, resulting in fixation of the cross pin 6 with respect to the pinning hole 5 without any cross pin 6 movement.

For a stem body 2 to be introduced in the femoral canal, the stem body 2 may be formed in a slightly tapered cylindrical shape at its distal portion 12 corresponding to the inner profile of the femoral canal.

Figure 6:
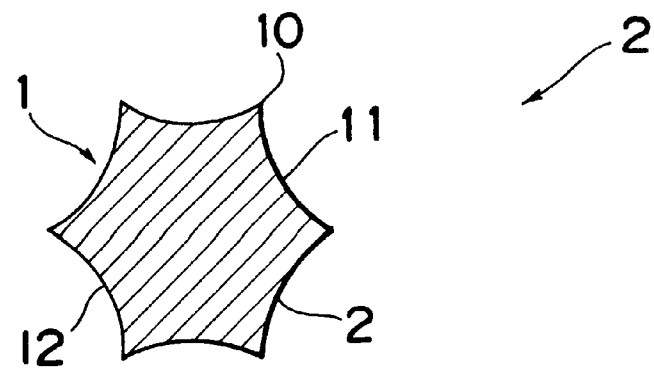

In another aspect of the present invention, the distal portion 12 of the stem body 2 may be selected to be made polygonal in cross section with a plurality of edges 10 and as many grooves 11 alternatingly and longitudinally aligned outside, as shown in FIG. 6. This configuration of the corrugated distal portion 12 of the stem member 2 can exhibit a great fixing force to connect the stem body 2 to the femur body from the earlier period of implanting. Thereafter, during the healing process, this corrugation can effectively promote the anchoring effect of the distal portion of the stem member due to the bone tissue growth and extension between the distal portion and the femur bone.

Thus, the present invention can adopt a combination of the above pinning mechanism to the corrugation profile of the stem member. The basic idea of the present invention for constituting a femoral prosthesis is to ensure the fixation at the proximally portion of the stem body due to the pinning mechanism and at the distal portion due to the specified profile.

Generally, distal portions of the femoral canals have high profile compliance to inserted prosthesis while the proximal portions of the femoral canals are poor in profile compliance because of different dimensions and profiles of the proximal femoral canal for each patient. Accordingly, it has been conventionally difficult to comply the stem body profile with the proximal inside of the femoral canal, even after having adjusted the outer shape of the stem body, resulting in the uncertain fixing of the prosthesis. In the present invention, by utilizing the cross pin 6 through the bone and through the stem body 2 to connect them, the cross pin 6 serves as a support point to greatly support both the stem body and the bone, independently of patient to patient differences.

The cross pin 6 stated above, also, has a feature of having have an high resistance to pulling of the stem body 2 out of the femoral canal since the cross pin 6 remains inserted into the opening which is formed in the bone wall, effectively to prevent the stem body from moving in the longitudinal direction of the bone.

Furthermore, it is advantageous that the pinning mechanism in the present invention can restrict relative micro-movement between the stem body 2 and the femur bone, since the cross pin 6 can be accurately made with a very narrow gap between the cross pin 6 and the pinning hole 5, and easily fit within the openings formed through the femur bone. Also, both the end portions of the cross pin 6 are supported under almost the same conditions by both sides of the femoral walls, so that fixing force to act between the femur bone and the stem body is balanced about the axis of the stem body 2, reducing deviation of the loads therebetween.

The present invention have been described according to the embodiments and accompanying drawings, but is not limited to the above embodiments. It will be apparent to those skilled in the art that modification may be made without departing from the true spirit and scope of the invention as set out in the following claims.

What is claimed is:

1. A femoral prosthesis, which comprises a stem body to be inserted into a femur bone, a neck portion fixed integrally at the proximal portion of the stem body, a spherical head member having an opening to receive the neck portion, and a cross pin for fixing the stem body to the femur bone, wherein the stem body is formed with a pinning hole through a proximal portion thereof corresponding to a greater trochanter of the femur bone, and the cross pin is in an unthreaded cylindrical shape inserted through the pinning hole with both ends of the cross pin projecting from the stem body to engage the wall of the femur bone.

2. A femoral prosthesis according to claim 1, wherein the stem body is formed with a bolt hole into the stem body below from a shoulder point of the stem body so as to reach the pinning hole and a bolt is inserted in the bolt hole to engage the cross pin which is held through the pinning hole.

3. A femoral prosthesis according to claim 2, wherein the cross pin is provided with a notch in a part of the surface of the cross pin at the midpoint of its length, the notch being capable of receiving the bolt.

4. A femoral prosthesis according to claim 3, wherein the bolt has a cylindrically tapered periphery at its middle portion which engages to the notch so as to enforce the cross pin toward an inner wall of the pinning hole, then fixing the cross pin and the pinning hole.

5. A femoral prosthesis according to claim 1, wherein the stem body has a distal portion which is polygonal in cross section with a plurality of edges and alternating grooves longitudinally aligned on an exterior surface of the distal portion.

6. A femoral prosthesis comprising:
   a stem body to be inserted into a femur bone;
   a neck portion fixed integrally at the proximal portion of the stem body;
   a spherical head member having an opening to receive the neck portion;
   a pinning hole through a proximal portion of the stem body corresponding positionally to a greater trochanter of the femur bone;
   a cross pin for fixing the stem body to the femur bone, the cross pin forming an unthreaded cylindrical shape with a notch formed on a surface at a midpoint of its length and inserted through the pinning hole with both ends projecting from the stem body to engage the wall of the femur bone; and
   a bolt hole disposed in the stem body so that a bolt inserted in the bolt hole engages the cross pin by means of the notch.

7. A femoral prosthesis according to claim 6, wherein the bolt has a cylindrically tapered portion at its middle portion to engage the notch so as to force the cross pin towards an inner wall of the pinning hole to fix the cross pin in the pinning hole.

8. A femoral prosthesis comprising:
   a stem body to be inserted into a femur bone;
   a distal portion of the stem body, polygonal in cross section, with a plurality of edges and alternating grooves longitudinally aligned on a surface thereof;
   a neck portion fixed integrally at the proximal portion of the stem body;
   a spherical head member having an opening to receive the neck portion;
   a pinning hole through a proximal portion of the stem body corresponding positionally to a greater trochanter of the femur bone;
   a cross pin for fixing the stem body to the femur bone, the cross pin forming an unthreaded cylindrical shape with a notch formed on a surface at a midpoint of its length and inserted through the pinning hole with both ends projecting from the stem body to engage the wall of the femur bone; and
   a bolt hole disposed in the stem body so that a bolt inserted in the bolt hole engages the cross pin by means of the notch.

9. A femoral prosthesis according to claim 8, wherein the bolt has a cylindrically tapered portion at its middle portion to engage the notch so as to force the cross pin towards an inner wall of the pinning hole to fix the cross pin in the pinning hole.

* * * * *